United States Patent
Hsu et al.

(10) Patent No.: US 6,733,773 B1
(45) Date of Patent: May 11, 2004

(54) PAPER PRODUCTS TREATED WITH OIL-IN-WATER EMULSIONS

(75) Inventors: Jay C. Hsu, Alpharetta, GA (US); Richard L. Shick, Alpharetta, GA (US); Audra S. Wright, Woodstock, GA (US); Joann A. Brooks, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/717,939

(22) Filed: Nov. 21, 2000

(51) Int. Cl.[7] .................................................. A61K 9/70
(52) U.S. Cl. ....................................... 424/443; 424/449
(58) Field of Search ................................ 424/443, 400

(56) References Cited

U.S. PATENT DOCUMENTS

| | | | |
|---|---|---|---|
| 3,188,165 A | 6/1965 | Magat et al. | |
| 4,190,643 A | 2/1980 | Watson et al. | |
| 4,309,469 A | 1/1982 | Varona | |
| 4,319,956 A | 3/1982 | Snyder et al. | |
| 4,362,781 A | 12/1982 | Anderson | |
| 4,462,981 A | 7/1984 | Smith | |
| 4,481,243 A | 11/1984 | Allen | |
| 4,559,157 A * | 12/1985 | Smith et al. | 424/401 |
| 4,690,821 A | 9/1987 | Smith et al. | |
| 4,690,825 A | 9/1987 | Won | |
| 4,764,418 A | 8/1988 | Kuenn et al. | |
| 4,786,367 A | 11/1988 | Bogart et al. | |
| 4,788,060 A | 11/1988 | Endicott et al. | |
| 4,824,689 A | 4/1989 | Kuenn et al. | |
| 4,882,221 A | 11/1989 | Bogart et al. | |
| 4,883,475 A | 11/1989 | Bogart et al. | |
| 4,943,350 A | 7/1990 | Bogart et al. | |
| 5,043,155 A | 8/1991 | Puchalski et al. | |
| 5,048,589 A | 9/1991 | Cook et al. | |
| 5,164,046 A | 11/1992 | Ampulski et al. | |
| 5,246,546 A | 9/1993 | Ampulski | |
| 5,252,332 A | 10/1993 | Goldstein | |
| 5,334,388 A | 8/1994 | Hoang et al. | |
| 5,336,212 A | 8/1994 | De Francesco | |
| 5,399,412 A | 3/1995 | Sudall et al. | |
| 5,510,001 A | 4/1996 | Hermans et al. | |
| 5,525,345 A | 6/1996 | Warner et al. | |
| 5,585,104 A | 12/1996 | Ha et al. | |
| 5,591,309 A | 1/1997 | Rugowski et al. | |
| 5,593,508 A | 1/1997 | Gatt et al. | |
| 5,601,871 A | 2/1997 | Krzysik et al. | |
| 5,614,293 A | 3/1997 | Krzysik et al. | |
| 5,624,676 A * | 4/1997 | Mackey et al. | 424/414 |
| 5,648,083 A * | 7/1997 | Blieszner et al. | 424/402 |
| 5,661,119 A | 8/1997 | Hersh et al. | |
| 5,665,364 A | 9/1997 | McAtee et al. | |
| 5,686,089 A | 11/1997 | Mitra et al. | |
| 5,705,164 A | 1/1998 | Mackey et al. | |
| 5,716,692 A * | 2/1998 | Warner et al. | 428/153 |
| 5,720,966 A | 2/1998 | Ostendorf | |
| 5,756,079 A | 5/1998 | Cauwet et al. | |
| 5,811,111 A | 9/1998 | McAtee et al. | |
| 5,830,487 A | 11/1998 | Klofta et al. | |
| 5,869,075 A * | 2/1999 | Krzysik | 424/414 |
| 5,871,763 A * | 2/1999 | Luu et al. | 424/402 |
| 5,885,697 A | 3/1999 | Krzysik et al. | |
| 5,891,835 A | 4/1999 | Vlasblom | |
| 5,916,568 A | 6/1999 | Smyth et al. | |
| 5,928,631 A | 7/1999 | Lucas et al. | |
| 5,942,240 A | 8/1999 | Merianos et al. | |
| 5,942,479 A | 8/1999 | Frankenbach et al. | |
| 5,948,416 A * | 9/1999 | Wagner et al. | 424/401 |
| 5,951,991 A | 9/1999 | Wagner et al. | |
| 5,962,001 A | 10/1999 | Rose et al. | |
| 5,976,555 A | 11/1999 | Liu et al. | |
| 6,001,377 A | 12/1999 | SaNogueira, Jr. et al. | |
| 6,013,271 A | 1/2000 | Doughty et al. | |
| 6,015,763 A | 1/2000 | Vlasblom | |
| 6,017,417 A | 1/2000 | Wendt et al. | |
| 6,025,431 A | 2/2000 | Cardinali et al. | |
| 6,046,378 A | 4/2000 | Quincy, III et al. | |
| 6,074,527 A | 6/2000 | Hsu et al. | |
| 6,093,410 A | 7/2000 | Peffly et al. | |
| 6,096,325 A | 8/2000 | Date et al. | |
| 6,107,537 A | 8/2000 | Elder et al. | |
| 6,120,783 A | 9/2000 | Roe et al. | |
| 6,153,208 A | 11/2000 | McAtee et al. | |
| 6,153,209 A | 11/2000 | Vega et al. | |
| 6,190,678 B1 | 2/2001 | Hasenoehrl et al. | |
| 6,200,594 B1 | 3/2001 | Ernest et al. | |
| 6,207,596 B1 | 3/2001 | Rourke et al. | |
| 6,217,889 B1 | 4/2001 | Lorenzi et al. | |
| 6,238,682 B1 | 5/2001 | Klofta et al. | |
| 6,267,975 B1 | 7/2001 | Smith, III et al. | |
| 6,280,757 B1 | 8/2001 | McAtee et al. | |
| 6,287,581 B1 | 9/2001 | Krzysik et al. | |
| 6,294,186 B1 | 9/2001 | Beerse et al. | |
| 6,338,855 B1 | 1/2002 | Albacarys et al. | |
| 2001/0018068 A1 | 8/2001 | Lorenzi et al. | |

FOREIGN PATENT DOCUMENTS

| | | |
|---|---|---|
| CA | 1113738 A | 12/1995 |
| DE | 3416043 A | 10/1985 |
| DE | 4202703 A1 | 8/1993 |
| EP | 613675 A1 | 9/1994 |
| EP | 365160 B1 | 12/1994 |
| EP | 808157 B1 | 11/1997 |
| EP | 0870496 A2 | 10/1998 |
| WO | WO 9321383 | 10/1993 |
| WO | WO 9405856 | 3/1994 |
| WO | WO 9614835 A1 | 5/1996 |
| WO | WO 9803147 | 1/1998 |
| WO | WO 9912519 A1 | 3/1999 |
| WO | WO 9921532 A1 | 5/1999 |
| WO | WO 9941068 | 8/1999 |
| WO | WO 9945971 | 9/1999 |
| WO | WO 0064408 A1 | 11/2000 |

* cited by examiner

Primary Examiner—Thurman K. Page
Assistant Examiner—Robert M. Joynes
(74) Attorney, Agent, or Firm—Dority & Manning, P.A.

(57) ABSTRACT

A paper product that is applied with a lotion composition is provided. In one embodiment of the present invention, the lotion composition includes water in an amount up to about 90% by weight of the lotion, an emollient component in an amount up to about 20% by weight of the lotion, a fatty alcohol component in an amount up to about 50% by weight of the lotion, an emulsifier component in an amount up to about 40% by weight of the lotion, and a skin conditioning component in an amount up to about 60% by weight of the lotion. Typically, the add-on level of the lotion composition is between about 1% to about 15% by weight of the paper product. As a result, the paper product can be used to dry the hands of a user, while also imparting certain benefits to the skin as well.

48 Claims, No Drawings

PAPER PRODUCTS TREATED WITH OIL-IN-WATER EMULSIONS

BACKGROUND OF THE INVENTION

Absorbent paper products, such as hand towels are commonly used to absorb fluids applied to the skin of a user during hand washing. The paper products are designed to absorb fluids from the skin and leave the skin dry. However, the soap ingredients often used to cleanse a person's hands or skin can remove oils, lipids, and natural skin conditioners and moisturizers from the stratum corneum of the person, leaving the skin excessively dry and subject to various skin problems, such as erythema, scales, flakes, and fissures. In addition, many people commonly wash their hands in environments susceptible to various diseases caused by the spread or growth of microbes, such as bacteria and viruses.

Various lotions have been developed to inhibit some of the skin problems mentioned above. In particular, these lotions are typically applied directly to the hands of a user when dry to soothe or moisten the skin. For example, one such lotion is sold under the tradename KimCare™ by Kimberly-Clark Corporation. The main ingredients of the KimCare™ lotion include water, cetearyl alcohol, dimethicone 200, caprylic/capric stearate triglyceride, $C_{12}$–$C_{15}$ alkyl benzoate, steareth-2, steareth-20, phospholipid SV, glycerin, chlorohexidene gluconate, and various other ingredients in trace amounts.

Although this lotion can provide numerous benefits to a user, it was thought that such a lotion could not be readily applied to paper products. In particular, it was thought that a paper product applied with such a lotion could not satisfactorily retain its absorbency characteristics so that it could still be used to dry a person's hands.

As such, a need currently exists for an absorbent paper product that can be applied with a lotion so that a person's skin can be simultaneously dried and moisturized or soothed by the lotion.

SUMMARY OF THE INVENTION

The present invention is directed to a paper product that can dry and condition the skin of a user. In accordance with one embodiment of the present invention, a lotion composition is applied to the paper product that contains water in an amount up to about 90% by weight of the lotion, an emollient component in an amount up to about 20% by weight of the lotion, a fatty alcohol component in an amount up to about 50% by weight of the lotion, an emulsifier component in an amount up to about 40% by weight of the lotion, and a skin conditioning component in an amount up to about 60% by weight of the lotion. Typically, the add-on level of the lotion is between about 1% to about 15% by weight of the paper product.

For example, in one embodiment of the present invention, the lotion applied to the paper product includes an emollient component (e.g., $C_{12}$–$C_{15}$ alkyl benzoate, etc.) in an amount between about 1% to about 15% by weight of the lotion.

Further, in this embodiment, the lotion also includes a fatty alcohol component in an amount between about 5% to about 40% by weight of the lotion. For instance, the fatty alcohol component can include cetyl alcohol, stearyl alcohol, cetearyl alcohol, arachidyl alcohol, behenyl alcohol, or combinations thereof. Moreover, the lotion also contain an emulsifier component in an amount between about 1% to about 30% by weight of the lotion. For instance, the emulsifier component can include at least one emulsifier, such as a polyoxyethylene stearyl ether. In addition, in this embodiment, a skin conditioning component is also included in an amount between about 5% to about 50% by weight of the lotion. For instance, the skin conditioning component, can include a humectant, such as glycerin.

In accordance with another embodiment of the present invention, a process for producing a paper product for drying and conditioning the skin of a user is disclosed. The process includes forming a fibrous web, through-drying the web to remove water therefrom, and thereafter treating the dried web with a lotion such that the lotion has an add-on level of between about 1% to about 15% by weight of said paper product. For example, in some embodiments, the lotion can be printed onto the paper web. In other embodiments, the lotion can also be sprayed onto the paper web.

It should be noted that any given range presented herein is intended to include any and all lesser included ranges. For example, a range of from 45–90 would also include 50–90; 45–80; 46–89 and the like. Thus, the range of 95% to 99.999% also includes, for example, the ranges of 96% to 99.1%, 96.3% to 99.7%, and 99.91 to 99.999%.

Other features and aspects of the present invention are discussed in greater detail below.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

In general, the present invention is directed to a paper product that contains a lotion useful for treating a person's skin. For example, the lotion can be an oil-in-water emulsion that is formed from a variety of ingredients. The emulsion includes water, an emollient component, a fatty alcohol component, an emulsifier component, a skin conditioning component (e.g., a humectant), and other optional ingredients (e.g., anti-microbial agents, preservatives, etc.). It has been discovered that the particular selection and amount of ingredients utilized in the lotion of the present invention can provide a synergistic effect when applied to a paper product. Moreover, it has also been discovered that the lotion of the present invention can be applied at relatively low add-on levels to a paper product such that the resulting paper product can remain absorbent. As a result, the paper product of the present invention can dry a person's skin after washing, while simultaneously imparting certain benefits to the skin, such as inhibiting microbial growth, skin disease, excessive skin dryness, etc.

Paper products made in accordance with the present invention can include various types of products, such as towels, wipes, napkins, facial and bath tissue, and the like. The paper product can generally be produced from paper webs having one or multiple layers. Moreover, depending on the desired characteristics, the paper product can contain one or multiple plies where each ply can contain one or more layers. The basis weight of the paper products can vary dependent on the particular application. In some embodiments, for example, the paper product can have a basis weight from about 1 to about 50 pounds per 2,880 square feet (i.e., ream), and in some embodiments, between about 5 to about 45 pounds per square ream. For instance, paper towels can sometimes be formed to have a basis weight of from about 10 to about 45 pounds per ream, and in some embodiments, between about 20 to about 30 pounds per ream. Suitable cellulosic fibers for use in connection with this invention include secondary (recycled) papermaking fibers and virgin papermaking fibers in all proportions. Such fibers include, without limitation, hardwood and softwood fibers as well as nonwoody fibers. Noncellulosic synthetic fibers can also be included as a portion of the furnish. It has been found that a high quality product having a unique balance of properties can be made using predominantly secondary fibers or all secondary fibers.

As stated above, the paper product of the present invention is applied with a lotion that contains a variety of components. For example, the lotion contains water. To ensure that the paper product can remain absorbent after being applied with the lotion, the water is typically present within the lotion in an amount up to about 90% by weight of the lotion, in some embodiments up to about 80% by weight of the lotion, in some embodiments between about 10% by weight to about 75% by weight of the lotion, and in some embodiments, between about 40% to about 70% by weight of the lotion.

In addition, the lotion utilized in the present invention also includes an emollient component that contains at least one emollient. For instance, some emollients that may be used include, but are not limited to, petroleum or mineral oils, such as petrolatum; animal oils, such as mink oil and lanolin oil; plant oils, such as sunflower oil, soy sterol, and avocado oil; silicone oils, such as alkyl methyl silicones; etc. Other suitable emollients may include PEG 75 lanolin, capric acid, caproic acid, caprylic acid, caprylic/capric mixed acids, caprylic/capric triglyceride (e.g., Crodamol GTCC sold by Croda, Inc.), cholesterol, lauric acid, magnesium stearate, myristic acid, oleic acid, palmitic acid, pentaerythritol, sorbitol, stearic acid, stearols (vegetable), methyl gluceth 20 benzoate, linear primary alkyl esters of benzoic acid (e.g., $C_{12}$–$C_{15}$ alkyl benzoate), ethoxylated cetyl stearyl alcohol, Finsolv® SLB 101 or SLB 201 (sold by Finitex Corp.). Still other suitable emollients are described in U.S. Pat. No. 4,559,157 to Smith et al., U.S. Pat. No. 4,690,821 to Smith et al., U.S. Pat. No. 5,830,487 to Klofta. et al., and U.S. Pat. No. 5,871,763 to Luu. et al., which are incorporated herein in their entirety by reference thereto for all purposes.

The amount of the emollient component in the composition can generally vary. For example, in some embodiments, the amount of the emollient component can be up to 20% by weight of the lotion, in some embodiments between about 1% to about 15% by weight of the lotion, and in some embodiments, between about 1% about 10% by weight of the lotion.

The use of an emollient component, such as described above, can provide a number of benefits to the lotion formed therefrom. For instance, the emollient component can act as a moisturizing agent when applied to the skin of a user. In particular, the emollient component can, in some cases, enhance the ability of a user's skin to retain water even after using the paper product. By retaining water, a user's skin will be less prone to becoming excessively dry, as well as being inhibited from developing certain skin problems, such as erythema. Moreover, the emollient component can help to maintain the soft, smooth, and pliable appearance of the skin by remaining on the skin surface or in the stratum corneum to act as a lubricant, to reduce flaking, and to improve the skin's appearance. For instance, in one embodiment, linear primary alkyl esters of benzoic acid, such as $C_{12}$–$C_{15}$ alkyl benzoate (e.g., Finsolv® TN sold by Finetex, Inc.) have been determined to be particularly effective in accomplishing these characteristics.

Besides an emollient component, the lotion of the present invention can also contain a variety of other materials. For example, as stated above, the lotion of the present invention also typically contains a fatty alcohol component that includes one or more fatty alcohols. For example, in one embodiment, three fatty alcohols can be utilized. Fatty alcohols can inhibit the emollient component deposited onto the surface of the paper product from substantially migrating into the interior of the paper. Thus, compared to paper products treated with some types of liquid formulations, a greater percentage of the resulting lotion of the present invention is retained on the surface of the paper product where it can contact and transfer to the user's skin to provide various benefits. Furthermore, a lower add-on level can be used to deliver the same benefits at a lower cost because of the efficient placement of the composition substantially at the surface of the product.

In general, the amount of the fatty alcohol component can vary depending on the amount of the emollient component utilized. For instance, in some embodiments, the amount of the fatty alcohol component in the composition can be up to about 50% by weight of the lotion, in some embodiments between about 5% to about 40% by weight of the lotion, and in some embodiments, between about 10% to about 30% by weight of the lotion. Moreover, suitable fatty alcohols can include, but are not limited to, alcohols having a carbon chain length of $C_{14}$–$C_{30}$, including, for example, cetyl alcohol, stearyl alcohol, cetearyl alcohol (which is a mixture of cetyl alcohol and stearyl alcohols), arachidyl alcohol, and behenyl alcohol. Other suitable fatty alcohols are described in U.S. Pat. No. 5,830,487 to Klofta. et al. and U.S. Pat. No. 5,871,763 to Luu. et al.

In some embodiments, for example, the inventors of the present invention have discovered that the combination of cetyl alcohol, stearyl alcohol, and cetearyl alcohol may be particularly useful as a fatty alcohol component for helping retain the lotion on the surface of the paper product such that it can be more readily transferred to the skin of a user. For instance, cetyl alcohol, stearyl alcohol, and cetearyl alcohol can each be present in an amount up to about 20% by weight of the lotion, and in some embodiments, between about 1% to about 10% by weight of the lotion.

Moreover, the lotion used in the present invention also contains an emulsifier component that contains at least one emulsifier to aid in dispersing the water and oil phases of the emulsion. The emulsifier component can be present within the lotion in an amount up to about 40% by weight of said lotion, in some embodiments between about 1% to about 30% by weight of said lotion, and in some embodiments, between about 5% to about 20% by weight of said lotion.

In general, any of a variety of emulsifiers can be utilized in the present invention. For example, nonionic, anionic, and/or cationic, emulsifiers are typically utilized in the present invention. Typically, the emulsifier or blend of emulsifiers has an overall hydrophilic-lipophilic balance (HLB) of at least about 8. However, it should be understood that emulsifiers and blends of emulsifiers having any other HLB value can also be utilized.

For instance, some nonionic emulsifiers that can be used in the emulsifier component include, but are not limited to, alkylene oxide esters of fatty acids, alkylene oxide diesters of fatty acids, alkylene oxide ethers of fatty acids, etc. Some examples of such alkylene oxide derived nonionic emulsifiers include, but are not limited to, ceteth-6, ceteth-10, ceteth-12, ceteareth-6, ceteareth-10, ceteareth-12, ceteareth-20, steareth-2, steareth-6, steareth-10, steareth-12, steareth-12, steareth-20, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, glycol stearate, propylene glycol stearate, glycol distearate, glyceryl laurate, glyceryl oleate, and mixtures thereof.

Other suitable nonionic emulsifiers suitable include sugar esters and polyesters, alkoxylated sugar esters and polyesters, polyhydroxy fatty acid amides, $C_1$–$C_{30}$ fatty acid esters of $C_1$–$C_{30}$ fatty alcohols, alkoxylated derivatives of $C_1$–$C_{30}$ fatty acid esters of $C_1$–$C_{30}$ fatty alcohols, alkoxylated ethers of $C_1$–$C_{30}$ fatty alcohols, polyglyceryl esters of $C_1$–$C_{30}$ fatty acids, $C_1$–$C_{30}$ esters of polyols, $C_1$–$C_{30}$ ethers of polyols, alkyl phosphates, polyoxyalkylene fatty ether phosphates, fatty acid amides, acyl lactylates, sorbitan esters, and mixtures thereof. Some examples of such emulsifiers include polyethylene glycol 20 sorbitan monolaurate (Polysorbate 20), polyethylene glycol 5 soy sterol, PPG-2 methyl glucose ether distearate, Polysorbate 80, cetyl phosphate, potassium cetyl phosphate, diethanolamine cetyl phosphate, Polysorbate 60, polyoxyethylene 20 sorbitan trioleate (Polysorbate 85), sorbitan monolaurate, polyoxyethylene 4 lauryl ether sodium stearate, polyglyceryl 4 isostearate, and mixtures thereof.

Besides the emulsifiers mentioned above, other types of nonionic emulsifiers, as well as other types of emulsifiers (e.g., cationic, anionic, polymeric, etc.), and blends thereof, can also be utilized. For instance, other suitable emulsifiers that can be utilized within the emulsifier component in accordance with the present invention are described in U.S. Pat. No. 6,001,377 to SaNogueira, Jr., et al., which is incorporated herein in its entirety by reference thereto for all purposes.

In one embodiment, it has been discovered that steareth-2 (polyoxyethylene-2 stearyl ether) and steareth-20 (polyoxyethylene-20 stearyl ether) and/or steareth-21 (polyoxyethylene-21 stearyl ether) may be particularly useful as emulsifiers within the emulsifier component of the lotion of the present invention. For instance, in one embodiment, steareth-2 and steareth-20 and/or steareth-21 can each be present in an amount up to about 20% by weight of the lotion, in some embodiments between about 1% to about 15% by weight of the lotion, and in some embodiments, between about 2% to about 10% by weight of the lotion.

Besides the above-mentioned components, a lotion used in the present invention also includes a skin conditioning component that contains one or more skin conditioning agents. A skin conditioning agent generally refers to any material that can enhance certain properties of the skin, such as by moisturizing the skin, softening the skin, protecting the skin, and the like. For example, skin conditioning agents can further moisturize a person's skin to inhibit excessive dryness and various related skin diseases. In some embodiments, the amount of the skin conditioning component can be up to about 60% by weight of the lotion, in some embodiments between about 5% to about 50% by weight of the lotion, and in some embodiments, between about 10% to about 40% by weight of the lotion.

For example, in one embodiment, the skin conditioning component can include a humectant (i.e., a compound that has an affinity for water). A humectant can generally provide a number of benefits to a lotion of the present invention. For example, as stated above, a lotion applied to a paper-product can be transferred to a person's hand after use. Because the lotion contains a humectant, which has an affinity for water, it can further enhance the retention of moisture on the person's skin and inhibit transepidermal water loss.

In general, a variety of humectants may be suitable for use in the present invention. Some examples of suitable humectants that can be used in the present invention include, but are not limited to, glycerin; ethoxylated glycerins, such as POE-26 glycerin, POE-7 glycerin, sorbitol, 1,2,6-hexanetriol sorbitol, and hydroxypropyl sorbitol; phosphinic carboxylic acid (PCA) and salts thereof, such as sodium PCA; alpha hydroxy acids and salts thereof, such as lactic acid, sodium lactate, and glycolic acid; glucose derivatives, such as glucose glutamate; polyalkylene glycols and alkylene polyols and their derivatives, including propylene glycol, dipropylene glycol, polypropylene glycol, polyethylene glycol, 1,3-butylene glycol, triethylene glycol, and dipropylene glycol; and other humectants, such as maltodextrin, maltitol, mannitol, zylitol, sodium polyaspartate, ethoxylated castor oil, various humectants available from Lipo Chemicals (e.g., acetamide MEA, ethoxylated glycerin, lactamide MEA, etc.), and the like. For instance, the inventors of the present invention have discovered that glycerin may be particularly useful in moisturizing the skin of a user and protecting it from excessive drying and other problems with the skin.

Moreover, the amount of humectant utilized in the lotion composition can vary. For example, in some embodiments, the amount of humectant can be up to about 20% by weight of the lotion, in some embodiments between about 1% to about 15% by weight of the lotion, and in some embodiments, between about 1% to about 10% by weight of the lotion.

Moreover, still other skin conditioning agents can also be utilized in the lotion composition. For instance, other skin conditioning agents that may be suitable for use in the present invention include, but are not limited to, dimethicone, glyceryl stearate, caprylic/capric stearate triglyceride, stearamidopropyl PG-dimonium chloride phosphate and cetyl alcohol (i.e., phospholipid SV), etc. Still other suitable skin conditioning agents are described in U.S. Pat. No. 4,559,157 to Smith et al., U.S. Pat. No. 4,690,821 to Smith et al., U.S. Pat. No. 5,830,487 to Klofta. et al., and U.S. Pat. No. 5,871,763 to Luu, et al., which are incorporated herein in their entirety by reference thereto for all purposes.

In one particular embodiment, the skin conditioning component contains glycerin; dimethicone; caprylic/capric stearate triglyceride; and stearamidopropyl PG-dimonium chloride phosphate and cetyl alcohol. For example, in some embodiments, the amount of glycerin, dimethicone, caprylic/capric stearate triglyceride, and stearamidopropyl PG-dimonium chloride phosphate and cetyl alcohol, can each be up to about 20% by weight of the lotion, in some embodiments between about 1% to about 15% by weight of the lotion, and in some embodiments, between about 1% to about 10% by weight of the lotion. It should also be understood that any of the ingredients mentioned above (e.g., emollient, fatty alcohol, etc.) and/or other ingredients can also act as skin conditioning agents as well.

As stated above, various other ingredients may also be utilized in the lotion of the present invention. For instance, in some embodiments, an antimicrobial agent (i.e., an additive that is capable of inhibiting the growth of viruses, bacteria, fungi, and other microbes) can be incorporated into the lotion composition to disinfect a user's skin and/or to inhibit the further spread of certain microbes. Typically, an antimicrobial agent utilized in the present invention is biocompatible. The antimicrobial agent can be soluble in the oil or water phases, or can reside in either phase as a suspension. For example, some suitable antimicrobial agents that can be used in the present invention include, but are not limited to, chlorohexidine gluconate; parachlorometaxylenol (PCMX); benzylthoneium chloride; chitosan, such as chitosan pyrrolidone carboxylate; 2,4,4'-trichloro-2'-hydroxydiphenyl ether (triclosan), etc. Other suitable antimicrobial agents are described in U.S. Pat. No. 5,871,763 to Luu, et al., U.S. Pat. No. 5,334,388 to Hoang, et al., and U.S. Pat. No. 5,686,089 to Mitra, et al., which are incorporated herein in their entirety by reference thereto for all purposes.

The amount of an antimicrobial agent(s) utilized in the lotion composition of the present invention can generally vary. For example, in some embodiments, the amount of the antimicrobial agent(s) can be up to about 20% by weight of the composition, in some embodiments up to about 10% by weight of the composition, and in some embodiments, between about 0.01% to about 5% by weight of the composition.

Furthermore, in some embodiments, the lotion can also contain one or more preservatives. The preservative(s) can inhibit the growth of certain microbes on the paper product before and/or after use. Moreover, when the lotion composition is transferred to the skin of a user, the preservative(s) can further inhibit the growth of microbes thereon. The amount of the preservative(s) utilized in the lotion composition of the present invention can generally vary. For example, in some embodiments, the amount of the preservative(s) can be up to about 5% by weight of the composition, in some embodiments up to about 3% by weight of the composition, and in some embodiments, between about 0.1% to about 2% by weight of the composition.

Some suitable preservatives that can be used in the present invention include, but are not limited to, Mackstat H 66 (available from McIntyre Group, Chicago, Ill.), DMDM hydantoin (e.g., Glydant Plus™, Lonza, Inc., Fair Lawn, N.J.), iodopropynyl butylcarbonate, Kathon (Rohm and Hass, Philadelphia, Pa.), methylparaben, propylparaben, 2-bromo-2-nitropropane-1,3-diol, benzoic acid, amidazolidinyl urea, diazolidinyl urea, and the like. Moreover, in one particular embodiment, a preservative obtained under the name "Phenonip" from NIPA Hardwick can be utilized. Other suitable preservatives includes those sold by Sutton Labs, such as "Germall 115" (amidazolidinyl urea), "Germall II" (diazolidinyl urea), and "Germall Plus" (diazolidinyl urea and iodopropynyl butylcarbonate).

In order to better enhance the benefits to consumers, other ingredients can also be used. For instance, some classes of ingredients that can be used include, but are not limited to: antiacne actives (a drug product used to reduce the number of acne blemishes, acne pimples, blackheads, and whiteheads); antifoaming agents (reduce the tendency of foaming during processing); antiseptic actives; antioxidants (product integrity); astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); opacifiers (reduce the clarity or transparent appearance of the product); skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); sunscreens (ingredients that absorb at least 85 percent of the light in the UV range at wavelengths from 290 to 320 nanometers, but transmit UV light at wavelengths longer than 320 nanometers); and emulsifiers (as cleansing agents, emulsifying agents, solubilizing agents, and/or suspending agents). For instance, in one embodiment, Aloe Vera powder can be utilized in an amount between about 0.0005% to about 0.005% by weight of the lotion.

Although various ingredients have been separately described herein, it should be understood that one ingredient may completely or partially accomplish the function of more than one ingredient. For example, an emollient utilized in the lotion of the present invention may also act as a skin conditioning agent.

Once formed, the lotion described above can then be applied to the paper product. The paper product may be formed from any papermaking process known in the art. For example, a papermaking process of the present invention can utilize creping, embossing, wet-pressing, double creping, calendering, as well as other known steps in forming the paper web. One particular embodiment of the present invention utilizes a non-compressive drying technique, such as uncreped through-drying, to form the paper product. In some instances, an uncreped through-dried paper product may have good absorbency and wet-resiliency characteristics. Some examples of uncreped through-drying techniques are disclosed in U.S. Pat. No. 5,048,589 to Cook, et al.; U.S. Pat. No. 5,399,412 to Sudall. et al.; U.S. Pat. No. 5,510,001 to Hermans. et al.; U.S. Pat. No. 5,591,309 to Rugowski. et al.; and U.S. Pat. No. 6,017,417 to Wendt, et al., which are incorporated herein in their entirety by reference thereto for all purposes.

For example, uncreped through-drying generally involves the steps of: (1) forming a furnish of cellulosic fibers, water, and optionally, other additives, such as debonders and wet-strength agents; (2) depositing the furnish on a traveling foraminous belt, thereby forming a fibrous web on top of the traveling foraminous belt; (3) subjecting the fibrous web to through-drying to remove the water from the fibrous web; and (4) removing the dried fibrous web from the traveling foraminous belt.

In some embodiments, once dried, the lotion described above can then be applied. In general, the lotion utilized in the present invention can be applied to the paper product using a variety of methods. For instance, in one embodiment, the lotion can be applied to the surface of the paper product using rotogravure printing, either direct or indirect (offset). Rotogravure printing can sometimes offer better control of the distribution and transfer rate of the lotion onto the paper product. In addition, other application methods, such as flexographic printing, spraying (e.g., WEKO), hot melt adhesive spraying (e.g., Nordson), blade, saturant, coating, droplet throw, and foam applications, can be used.

Further, the lotion can be applied to one or both outer surfaces of the product after the product has been dried. When utilizing a multi-ply paper product, the lotion can be applied after the plies are brought together or prior to bringing the plies together. The individual plies can be layered or blended (homogeneous), creped or uncreped, through-dried or wet-pressed. In one embodiment, for example, the paper product is an uncreped through-dried paper product.

Other methods of applying the lotion to a paper product can also be utilized. For example, some ingredients of the lotion can be first entrapped within a porous delivery vehicle before being applied to the paper product such that the ingredients can be controllably released during drying and after the lotion is transferred to a users skin. For instance, some delivery vehicles that can be used include, but are not limited to, microsponges, microcapsules, cyclodextrins and their derivatives, liposomes, polymeric sponges, and spray-dried starch. For instance, in some embodiments, the lotion may contain microcapsules in an amount of up to about 25% by weight of the lotion, in some embodiments up to about 10% by weight of the lotion, and in some embodiments, between about 0.2% to about 5% by weight of the lotion.

For instance, some examples of "microsponges" are describe in U.S. Pat. No. 4,690,825 to Won, which is incorporated herein in its entirety by reference thereto for all purposes. Another delivery vehicle that may be useful is a sponge-like material, such as POLY-PORE® L200. Moreover, one example of a microcapsule that may be suitable for use in the present invention is POLY-PORE® E200 (Chemdal Corp., Arlington Heights, Ill.), which is a delivery agent having soft, hollow spheres that can contain an additive at over 10 times the weight of the delivery vehicle.

The add-on level of the lotion can generally vary depending on the desired effect of the lotion on the product attributes and the specific composition. As used herein, the term "add-on level" refers to the weight of a paper product treated with the lotion subtracted by the weight of the paper product prior to treatment, wherein this calculated weight is divided by the weight of the treated paper product and then multiplied by 100. For example, the add-on level of the composition can be from about 1 to about 15 weight percent, in some embodiments from about 1 to about 10 weight percent, and in some embodiments, from about 1 to about 5 weight percent, based on the weight of the paper product.

The present invention may be better understood with reference to the following example.

EXAMPLE

The ability of a paper product to condition the skin of a user during drying was demonstrated. A lotion was first formed from a water phase and an oil phase. In particular, the lotion had the following composition:

TABLE 1

Components of the Lotion

| Component | Weight % of the Lotion |
|---|---|
| Phase A | |
| Water | 67.336 |
| Glycerin | 4.000 |
| Phase B | |
| $C_{12}$–$C_{15}$ alkyl benzoate | 4.000 |
| Cetearyl alcohol | 7.000 |
| Caprylic/capric stearate triglyceride | 4.000 |
| Steareth-2 | 2.400 |
| Steareth-20 | 1.800 |
| Stearamidopropyl PG-dimonium chloride phosphate and cetyl alcohol | 4.000 |
| Dimethicone | 4.000 |
| Methylparaben | 0.400 |
| Panthenol (vitamin B-5) | 0.002 |
| Tocopheryl acetate (vitamin E) | 0.002 |
| Preservative | 1.000 |
| Fragrance | 0.060 |

The lotion composition was prepared by first combining the ingredients of Phase A at a temperature of 75° C. and separately combining the ingredients of Phase B at a temperature of 75° C. Thereafter, Phase B was added to Phase A using vigorous stirring (i.e., 1500 revolutions per minute), which was continued for 10 minutes. The stirring speed was then slightly reduced (i.e., 1000 revolution per minute) and further mixed for 10 minutes. Once mixed, the ingredients were placed into a water bath at room temperature (i.e., between about 5° C. to about 25° C.) and allowed to cool to room temperature while being stirred at about 300 to 400 revolutions per minute.

Once formed, the resulting lotion was sprayed onto an uncreped through-dried hand towel that was formed in a manner such as described above such that the add-on level was 10% by weight of the hand towel. The towel was formed from recycled fibers in an amount of 50% by weight of the web and from Pictou northern softwood fibers in an amount of 50% by weight of the web. The Pictou fibers were refined for B minutes using conventional refining techniques. The furnishes were then supplied to a machine chest and blended. A Kymene® 557H wet strength agent was also added to the machine chest in an amount of 20 pounds per ton. Further, a Witco C-6001 imidazoline-based softener was applied to the machine chest thereafter in an amount of 1.5 pounds per ton. The fibrous furnish was then formed into a paper web and dried using a through-air dryer. The resulting hand towel had a basis weight of 25 pounds per ream.

After forming the hand towel, the properties of the hand towel were compared to an untreated hand towel using the following procedure. Initially, 14 nurses washed their hands four times with IVORY® Bar Soap and dried them with the untreated towel that was folded. During each wash, the hands of the nurses were thoroughly washed and lathered for 15 seconds.

Thereafter, the subjects then washed their hands four additional times and dried them with the hand towel of the present invention. The number of towels used after the first and fourth washes was recorded. After a five minute waiting period, the nurses washed their hands four additional times. Finally, the nurses were asked to compare the overall hand feel and drying ability of each towel.

Table 2 reflects the percent of those tested who only used the corresponding number of towels to dry their hands after the first and fourth washes for the untreated sample.

TABLE 2

Towel Usage (untreated sample)

| Number of Towels Used | (%) First Wash | (%) Fourth Wash |
|---|---|---|
| 1 | 9.0 | 0.0 |
| 2 | 79.0 | 91.0 |
| 3 | 12.0 | 9.0 |
| 4 | 0.0 | 0.0 |

Table 3 reflects the percent of those tested who only used the corresponding number of towels to dry their hands after the first and fourth washes for the treated sample.

TABLE 3

Towel Usage (treated sample)

| Number of Towels Used | (%) First Wash | (%) Fourth Wash |
|---|---|---|
| 1 | 0.0 | 0.0 |
| 2 | 79.0 | 79.0 |
| 3 | 21.0 | 21.0 |
| 4 | 0.0 | 0.0 |

As illustrated from the Tables 2 and 3, the addition of the lotion composition onto a hand towel did not substantially affect the ability of the towel to dry a person's hands. For example, the percentage of the subjects that needed three towels to dry their hands for the first wash only increased from 12.0% to 21.0%.

In addition, various other attributes of the hands of the subjects after using the samples are also given below in Table 4.

TABLE 4

Hand Attributes

| Attribute | % Who Preferred Untreated Towel | % Who Preferred Treated Towel | % Who Perceived No Difference in Samples |
|---|---|---|---|
| Lotionized | 0.0 | 91.0 | 9.0 |
| Softness | 3.0 | 88.0 | 9.0 |
| Smoothness | 3.0 | 88.0 | 9.0 |
| Silkiness | 0.0 | 88.0 | 12.0 |
| Moisturization | 0.0 | 94.0 | 6.0 |
| Overall Hand Condition | 0.0 | 94.0 | 6.0 |

As indicated above, the hand towel of the present invention can impart a number of beneficial affects to the user of a skin when used.

Moreover, the ability of the lotion to affect the moisture and skin barrier properties of skin was also tested. In particular, nine subjects were first acclimated in a controlled room set at 70° F. and 50% relative humidity for 20 minutes. Upon acclimation, each subject had four 63 $cm^2$ test sites outlined on their volar forearm using a standard template. A series of baseline measurements were then taken from each test site with a Skicon-200 Conductance Meter (measurement of skin hydration) and a DermaLab® Systems Instrument (measurement of skin barrier damage). With the Skicon Meter, five conductance readings were taken for each 63 $cm^2$ test site and averaged. With the DermaLab® Instrument, four readings per second were taken at each test site and averaged.

The test sites were then washed with Ivory® Bar soap and dried with the appropriate hand towel (untreated and treated with the lotion of Table 2). To wash, the technician wet the site for 10 seconds, lathered for 30 seconds with Ivory® soap using a circular motion with the first two fingers, rinsed for 15 seconds or more if necessary until site was completely free of soap. For wiping, each towel was folded into quarters and then folded into eighths. The test site was wiped using a downward motion with one side of the vertically held towel turned over to wipe with other side. The technician started at the top of each site with hands adjacent to each other to make a downswing motion to assure that as much of the towel contacted the test site as possible. The site was wet with water (for 5 seconds) and the towel then turned to the next ¼ area. Drying steps were repeated 3 more times, as described above, to ensure that the entire towel was used.

This procedure was repeated every fifteen minutes, four times per day, for four consecutive days. One hour after the final wash, measurements were taken using the Skicon-200 Conductance Meter and the DermaLab® Systems Instrument. A total of 4 untreated towels and 4 treated towels was used each day. On the fifth day, only baseline readings were taken. The Skicon results are shown below in Table 5 and the DermaLab® results are shown in Table 6.

The data shown in Tables 5 and 6 represents the average percent change from the Day 1 base line, before washing each day (referred to as "b") and after the final wash of a day (referred to as "a"), over the five-day time period for the untreated and treated towels. A decrease in SkiCon values from the baseline represents a decrease in skin hydration properties, while an increase in DermaLab® values from the baseline represents an increase in skin barrier damage.

TABLE 5

Skicon Results (Skin Hydration Properties)

| | Day 1 | Day 2 (b) | Day 2 (a) | Day 3 (b) | Day 3 (a) | Day 4 (b) | Day 4 (a) | Day 5 (b) |
|---|---|---|---|---|---|---|---|---|
| Untreated Towel | −18% | −6% | −10% | +14% | +5% | −15% | −21% | −21% |
| Treated Towel | +10% | 0% | −15% | +6% | −2% | −11% | −31% | −16% |

As shown in Table 5, the towel treated according to the present invention exhibited improved moisture conductance compared to the untreated towel. For instance, after five days, the untreated towel had 21% less moisture conductance than the initial baseline moisture conductance, while the treated towel had only 16% less moisture conductance.

TABLE 6

DermLab ® Results (Skin Barrier Damage Properties)

|  | Day 1 | Day 2 (b) | Day 2 (a) | Day 3 (b) | Day 3 (a) | Day 4 (b) | Day 4 (a) | Day 5 (b) |
|---|---|---|---|---|---|---|---|---|
| Untreated Towel | 62% | 62% | 202% | 228% | 401% | 323% | 414% | 314% |
| Treated Towel | 29% | 37% | 78% | 108% | 184% | 161% | 224% | 193% |

As shown in Table 6, the towel treated according to the present invention exhibited improved skin barrier properties compared to the untreated towel. For instance, after five days, the untreated towel had a 314% increase in skin barrier damage from the initial baseline reading, while the treated towel had an increase of only 193%.

Thus, as indicated from the representative example above, a paper product of the present invention can provide numerous benefits to a user. Specifically, it has been discovered that the particular selection and amount of ingredients utilized in the lotion of the present invention can provide a synergistic effect when applied to a paper product. For instance, the lotion applied to the paper product can help moisturize the skin of a user during use, as well as remaining on a user's hands for continued moisturizing affects. In some cases, the lotion can enhance the ability of a user's skin to retain water even after using the paper product. By retaining water, a user's skin can be prevented from becoming excessively dry, as well as being inhibited from developing certain skin problems, such as erythema. Moreover, the lotion can help to maintain the soft, smooth, and pliable appearance of the skin by its ability to remain on the skin surface or in the stratum corneum to act as a lubricant, to reduce flaking, and to improve the skin's appearance. In some instances, the lotion can even help disinfect the skin of a user to inhibit the growth and/or spreading of various microbes.

In addition, as a result of the lower lotion add-on level that is obtainable in accordance with the present invention, a paper product formed therewith can also retain the ability to dry a person's skin. Thus, for example, a person can initially wash his/her hands using conventional soap. Thereafter, the person can utilize a paper product of the present invention for drying the wetted skin.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent paper product for drying and conditioning the skin of a user, said paper product comprising:
   a paper web; and
   an oil-in-water emulsified lotion applied to said paper web such that the add-on level of said lotion is between about 1% to about 15% by weight of said paper product, said lotion consisting essentially of:
   i) water in an amount between about 10% to about 75% by weight of said lotion;
   ii) an emollient component in an amount between about 1% to about 15% by weight of said lotion;
   iii) a fatty alcohol component in an amount between about 5% to about 40% by weight of said lotion;
   iv) an emulsifier component in an amount between about 1% to about 30% by weight of said lotion; and
   v) a skin conditioning component comprising between about 5% to about 50% by weight of said lotion, said skin conditioning component including glycerin in an amount between about 1% to about 10% by weight of said lotion.

2. A paper product as defined in claim 1, wherein said water comprises between about 40% to about 70% by weight of said lotion.

3. A paper product as defined in claim 1, wherein said emollient component comprises between about 1% to about 10% by weight of said lotion.

4. A paper product as defined in claim 1, wherein said emollient component includes a linear primary alkyl ester of benzoic acid.

5. A paper product as defined in claim 4, wherein said linear primary alkyl ester of benzoic acid is $C_{12}$–$C_{15}$ alkyl benzoate.

6. A paper product as defined in claim 1, wherein said fatty alcohol component comprises between about 10% to about 30% by weight of said lotion.

7. A paper product as defined in claim 1, wherein said fatty alcohol component includes a fatty alcohol selected from the group consisting of cetyl alcohol, stearyl alcohol, cetearyl alcohol, arachidyl alcohol, behenyl alcohol, and combinations thereof.

8. A paper product as defined in claim 1, wherein said emulsifier component comprises between about 5% to about 20% by weight of said lotion.

9. A paper product as defined in claim 1, wherein said emulsifier component includes a polyoxyethylene stearyl ether.

10. A paper product as defined in claim 1, wherein said skin conditioning component comprises between about 10% to about 40% by weight of said lotion.

11. A paper product as defined in claim 1, wherein said skin conditioning component includes a skin conditioning agent selected from the group consisting of dimethicone, glyceryl stearate, caprylic/capric stearate triglyceride, stearamidopropyl PG-dimonium chloride phosphate and cetyl alcohol, and combinations thereof.

12. A paper product as defined in claim 1, wherein said add-on level of said lotion is between about 1% to about 10% by weight of said paper product.

13. A paper product as defined in claim 1, wherein said lotion further comprises an antimicrobial agent, a preservative, or combinations thereof.

14. A paper product as defined in claim 1, wherein said paper product is a towel having a basis weight between about 1 to about 50 pounds per ream.

15. A paper product as defined in claim 1, wherein said paper product is a towel having a basis weight between about 15 to about 45 pounds per ream.

16. An absorbent paper towel for drying and conditioning the skin of a user, said towel having a basis weight from about 15 to about 45 pounds per ream, said towel comprising:
a paper web;
an oil-in-water emulsified lotion applied to said paper web such that the add-on level of said lotion is between about 1% to about 10% by weight of said paper towel, said lotion comprising;
i) water in an amount between about 10% to about 75% by weight of said lotion;
ii) an emollient component in an amount between about 1% to about 15% by weight of said lotion, said emollient component including $C_{12}$–$C_{15}$ alkyl benzoate;
iii) a fatty alcohol component in an amount between about 5% to about 40% by weight of said lotion, wherein said fatty alcohol component includes a fatty alcohol selected from the group consisting of cetyl alcohol, stearyl alcohol, cetearyl alcohol, arachidyl alcohol, behenyl alcohol, and combinations thereof;
iv) an emulsifier component in an amount between about 1% to about 30% by weight of said lotion, said emulsifier component including at least one emulsifier; and
v) a skin conditioning component in an amount between about 5% to about 50% by weight of said lotion, said skin conditioning component including glycerin in an amount of between about 1% to about 10% by weight of said lotion.

17. A paper towel as defined in claim 16, wherein said water comprises between about 40% to about 70% by weight of said lotion.

18. A paper towel as defined in claim 16, wherein said emollient component comprises between about 1% to about 10% by weight of said lotion.

19. A paper towel as defined in claim 16, wherein said fatty alcohol component comprises between about 10% to about 30% by weight of said lotion.

20. A paper towel as defined in claim 16, wherein said emulsifier component comprises between about 5% to about 20% by weight of said lotion.

21. A paper towel as defined in claim 16, wherein said emulsifier includes a polyoxyethylene stearyl ether.

22. A paper towel as defined in claim 16, wherein said skin conditioning component comprises between about 10% to about 40% by weight of said lotion.

23. A paper towel as defined in claim 16, wherein said skin conditioning component includes a skin conditioning agent selected from the group consisting of dimethicone, glyceryl stearate, caprylic/capric stearate triglyceride, stearamidopropyl PG-dimonium chloride phosphate and cetyl alcohol, and combinations thereof.

24. A paper towel as defined in claim 16, wherein said lotion further comprises an antimicrobial agent, a preservative, or combinations thereof.

25. A method for forming a paper product for drying and conditioning the skin of a user, said method comprising:
forming a web from at least one furnish containing fibers and water;
through-drying said web to remove water therefrom; and thereafter, treating said dried web with an oil-in-water emulsified lotion such that said lotion has an add-on level of between about 1% to about 15% by weight of said paper product, said lotion consisting essentially of:
i) water in an amount between about 10% to about 75% by weight of said lotion;
ii) an emollient component in an amount between about 1% to about 15% by weight of said lotion;
iii) a fatty alcohol component in an amount between about 5% to about 40% by weight of said lotion;
iv) an emulsifier component in an amount between about 1% to about 30% by weight of said lotion; and
v) a skin conditioning component comprising between about 5% to about 50% by weight of said lotion, said skin conditioning component including glycerin in an amount between about 1% to about 10% by weight of said lotion.

26. A method as defined in claim 25, wherein said lotion is printed onto said paper web.

27. A method as defined in claim 25, wherein said lotion is sprayed onto said paper web.

28. A method as defined in claim 25, wherein said water comprises between about 40% to about 70% by weight of said lotion.

29. A method as defined in claim 25, wherein said emollient component comprises between about 1% to about 10% by weight of said lotion.

30. A method as defined in claim 25, wherein said emollient component includes a linear primary alkyl ester of benzoic acid.

31. A method as defined in claim 30, wherein said linear primary alkyl ester of benzoic acid is $C_{12}$–$C_{15}$ alkyl benzoate.

32. A method as defined in claim 25, wherein said fatty alcohol component comprises between about 10% to about 30% by weight of said lotion.

33. A method as defined in claim 25, wherein said fatty alcohol component includes a fatty alcohol selected from the group consisting of cetyl alcohol, stearyl alcohol, cetearyl alcohol, arachidyl alcohol, behenyl alcohol, and combinations thereof.

34. A method as defined in claim 25, wherein said emulsifier component comprises between about 5% to about 20% by weight of said lotion.

35. A method as defined in claim 25, wherein said emulsifier component includes a polyoxyethylene stearyl ether.

36. A method as defined in claim 25, wherein said skin conditioning component comprises between about 10% to about 40% by weight of said lotion.

37. A method as defined in claim 25, wherein said skin conditioning component includes a skin conditioning agent selected from the group consisting of dimethicone, glyceryl stearate, caprylic/capric stearate triglyceride, stearamidopropyl PG-dimonium chloride phosphate and cetyl alcohol, and combinations thereof.

38. A method as defined in claim 25, wherein said add-on level of said lotion is between about 1% to about 10% by weight of said paper product.

39. A method as defined in claim 25, wherein said lotion further comprises an antimicrobial agent, a preservative, or combinations thereof.

40. A method as defined in claim 25, wherein said paper product is a towel having a basis weight between about 15 to about 45 pounds per ream.

41. An absorbent paper towel as defined in claim 16, wherein said paper web is formed by uncreped, through-drying.

42. An absorbent paper product as defined in claim 1, wherein said paper web is formed by uncreped, through-drying.

43. A method as defined in claim 25, wherein said paper web is formed without being creped.

44. A method as defined in claim 25, wherein the fibers contain secondary fibers.

45. A paper towel as defined in claim 16, wherein the paper web contains secondary fibers.

46. A paper product as defined in claim 1, wherein the paper web contains secondary fibers.

47. A paper product as defined in claim 1, wherein said lotion further comprises a fragrance, vitamin B-5, vitamin E, or combinations thereof.

48. A method as defined in claim 25, wherein said lotion further comprises a fragrance, vitamin B-5, vitamin E, or combinations thereof.

* * * * *